United States Patent [19]

Lee

[11] 4,352,663

[45] Oct. 5, 1982

[54] METHOD AND APPARATUS FOR SETTING A DENTAL ARTICULATOR

[76] Inventor: Robert L. Lee, 22937 Grand Ter., Colton, Calif. 92324

[21] Appl. No.: 147,631

[22] Filed: May 7, 1980

[51] Int. Cl.³ .............................................. A61C 19/04
[52] U.S. Cl. ........................................ 433/73; 433/72; 433/56; 33/174 D
[58] Field of Search ........................ 433/56, 72, 73, 69, 433/68, 75; 33/1 N, 174 D

[56] References Cited

U.S. PATENT DOCUMENTS

| | | | |
|---|---|---|---|
| 667,570 | 2/1901 | Penfield | 33/1 N |
| 1,033,562 | 7/1912 | Eltner | 433/56 |
| 1,532,878 | 4/1925 | Bugbee | 33/1 N |
| 3,130,494 | 4/1964 | MacKay | 433/69 |
| 3,159,914 | 12/1964 | DePietro | 433/56 |
| 4,034,475 | 7/1977 | Lee | 433/56 |

OTHER PUBLICATIONS

"The Problem of Articulation", by Gysi, Dental Cosmos, vol. LII-1, pp. 1-19, vol. LII-1, pp. 149-169, vol. LII-10, pp. 269-283.

*Primary Examiner*—Gene Mancene
*Assistant Examiner*—John J. Wilson
*Attorney, Agent, or Firm*—Knobbe, Martens, Olson, Hubbard & Bear

[57] ABSTRACT

A protractor-comparator type tool is used to determine characteristics of a recorded path of a patient's jaw movement for purposes of setting a dental articulator.

4 Claims, 3 Drawing Figures

METHOD AND APPARATUS FOR SETTING A DENTAL ARTICULATOR

FIELD OF THE INVENTION

This invention relates to an improved method and apparatus for measuring jaw movements and setting a dental articulator.

BACKGROUND OF THE INVENTION

U.S. Pat. No. 4,034,475 discloses a system wherein jaw movements are recorded on a small sheet or plate overlying a patient's temporo-mandibular joint, and that information is then used to position preformed guide blocks in a dental articulator. Such blocks have average value guide openings for receiving the styluses of the articulator which define or represent a hinge axis.

In one approach the recorded curve of protrusive path is traced onto a transparent sheet which is then mounted on the upper frame of a dental articulator so that the patient's hinge axis is aligned with the axis defined by the styluses of the lower frame of a dental articulator. A reference line on the recorded plate which was in the patient's horizontal reference plane when the protrusive path was recorded is aligned with a corresponding reference plane on the dental articulator. The analogue guide blocks in the upper frame of the articulator which receive the styluses of the lower frame each have a curved upper wall which determines the protrusive path and operation of the articulator. The curve, which has a radius close to that of a significant percentage of the population, is marked on the exterior of the guide block in some suitable fashion. To complete the setting of the guide block in the articulator, the guide block is rotated until the curve on its exterior surface is aligned with the curve representing the patient's protrusive path which is marked on the tracing that is positioned adjacent the curve on the guide block. Once the curves are aligned, as best as they can be, the guide block is fixed in that position, followed by setting of the guide block on the other side of the articulator. The operation of the articulator is then used to simulate the patient's jaw movements.

While the above-described system has many advantages over systems that had previously been used for making jaw movement measurements and for setting dental articulators, the several steps take time and are sources for error. For example, the simplest way of obtaining the tracing of the patient's protrusive curve on the transparent sheet is to position the transparency over the record plate and manually trace the curve onto the transparency. While this is direct, it is dependent to some extent on the skill and care of the operator. Secondly, means must be provided on the dental articulator for mounting the transparency on the articulator in proper position with respect to the articulator horizontal plane of reference. The above-mentioned patent discloses a special fixture for this purpose which is temporarily mounted on the upper frame of the articulator and then removed after the guide blocks have been properly set. This of course introduces some equipment expense and adds to the time required to set the articulator. There is also the expense of marking or indicating on the exterior of the guide block the curvature of the upper wall of the guide block.

Gysi, as recorded in the January 1910 issue of the Dental Cosmos discloses a dental articulator wherein a pair of guide plates each having curved paths formed therein are used to guide a horizontal shaft which is part of the upper frame of a dental articulator. The curved slots are said to be average value representations of movements of a patient's lower jaw. Paths of a patient's jaw movements are obtained on a record card, and by trial and error, the guide plate having a curved slot most closely conforming to that of the recorded path is physically aligned over the recorded path. Two pointers on the plate define a line which is approximately parallel to a central portion of the curved slot. Points at tips of the pointers are marked on the recording sheet; and after the guide plate is removed from the sheet, a line is drawn between the two points and extended to intersect the lower edge of the recording sheet, to form an angle with respect to the lower edge. The lower edge was positioned parallel to the plane of occlusion of the patient's jaws when the paths of mandibular movement were recorded on the sheet. Thus, the angle formed on the card is an angle of a portion of a mandibular movement curve with respect to the plane of occlusion. A protractor is then used to measure the angle, and this measurement is used to set the angle of the guide plates when they are mounted on a dental articulator.

Although there are some advantages to the Gysi system, there are also some shortcomings. The line defined by the pointers on the Gysi guide plate is somewhat arbitrarily positioned in that it varies as the curve varies. Further, the system requires marking a measurement with the protractor after the angle has been formed; and the angle obtained is with respect to the plane of occlusion rather than with respect to a plane through the patient's hinge axis. More importantly, the Gysi articulator is not of the type currently being used.

SUMMARY OF THE INVENTION

In accordance with the present invention the need for the separate transparency mentioned in U.S. Pat. No. 4,034,475 is eliminated. The special fixture to be mounted on the articulator for holding the tracing is eliminated, and the need for marking the guide block curvature on the exterior of the guide block is eliminated. To replace these items and the corresponding steps during use of the system, there is provided a tool, which in its preferred form is somewhat of a combination comparator and protractor, that is used to obtain the necessary information from the recording of the patient's protrusive path to set the articulator guide blocks.

Broadly stated, the tool is provided with a curve which corresponds or represents a curved surface on an articulator guide frame which controls the movement of a mating frame. The tool is further formed with means defining one or more scale lines representing reference lines with respect to the tool curve. In use, the curve on the tool is aligned with the curve of the patient's jaw movement, and the orientation of the reference line on the recording is observed with respect to a scale line on the tool. This observation may then be used to position directly the guide in the articulator. This is done without need for any measurement or drawing of additional lines.

The tool must be designed to be coordinated with a particular type of articulator and jaw movement recording. With a system of the type disclosed in the above mentioned patent, a representation of the curve or protrusive path of an articulator stylus when it is engaging the upper wall of the guide block opening is provided on the tool. Preferably, the tool is a thin, flat, transparent member and the curve is scribed or otherwise marked thereon. The tool is further provided with appropriate means defining a reference or scale line with respect to the curve that corresponds to a line through the hinge axis of the curve and represents a horizontal plane of reference in the articulator. After a recording of a patient's protrusive movement is made on a thin grid sheet, it is normally removed and mounted on a patient's record card. The tool is positioned on top of the record card, and the tool moved until its curve is properly aligned with the curve on the record sheet. The angular difference between the scaleline on the tool and the reference line on the tracing can then be observed and read by suitable indicia, preferably on the tool, that correspond to angular settings of the guide blocks on the articulator. Thus, it is only necessary to set the guide block at the observed angle. In this way, the accuracy of aligning the patient's recorded path directly with respect to the curve of the guide block is maintained and yet the information is obtained in a simple and direct manner eliminating some of the hardware and measuring steps previously used.

SUMMARY OF THE DRAWINGS

With reference to FIG. 1, the tool of the invention may be seen to be a thin flat member 14 made of transparent, plastic or other suitable material. A right curve 16 and a left curve 18 are scribed or otherwise formed on one surface of the member 14. As can be seen, the curves intersect or terminate at their upper ends at the central portion of the tool. A series of scale or reference lines radiate outwardly from the intersection 19 of the curves 18 and 16, although they are not shown actually extending through point 19.

Figure 3:
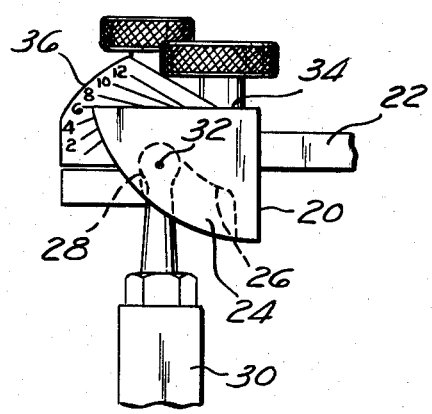
FIG. 3 is a view of the right portion of a dental articulator illustrating the setting of the angular orientation of a guide block in an articulator, based on the information received from utilizing the tool as shown in FIG. 2.

The curves correspond to the curved upper wall of the opening in right and left articulator guide blocks. An example of right guide block 20 is shown in FIG. 3, the guide block being rotatably mounted in the upper frame 22 of dental articulator. An opening 24 is formed within the guide block 20, and the upper wall 26 of the opening has a curvature which guides the protrusive movement of the articulator frames. The guide block 16 is supported on a spherical stylus 28 mounted on a pedestal 30 forming a part of the lower frame of the articulator. Further details of such an articulator may be obtained by reference to the above-mentioned U.S. Pat. No. 4,034,475.

As is well known, the upper and lower frames of an articulator may be moved in a manner to simulate jaw movement. In so doing, the movement of the upper and lower frames relative to each other is guided by the spherical stylus 28 moving within the opening 24. In particular, the protrusive movement is guided by the stylus 28 engaging the upper surface 26 of the guide block. In the position shown, the stylus is in centric relation position with respect to the guide block opening 24. In that position, the hinge axis 32 of the stylus 28 is aligned with the rotational axis of the guide block 20. That is, the block is fixed to a pin (not shown) which is rotatably mounted in the upper frame and the axis of the pin is co-axial with the stylus hinge axis 32. In referring to FIG. 3, the axis 32 is actually at the center of the spherical stylus, and thus the wall 26 of the guide block is actually spaced from but parallel to the path of the center of the stylus.

The upper edge 34 of the guide block 20 is utilized as a reference line for making the angular setting of the guide block. As the guide block is rotated the upper edge of the guide block moves with relation to the vertical lug 36 having the scale numbered lines thereon for use in setting the angular orientation of the guide block. In the illustration of FIG. 3, the scale line 6 is aligned with the block upper edge.

Figure 1:
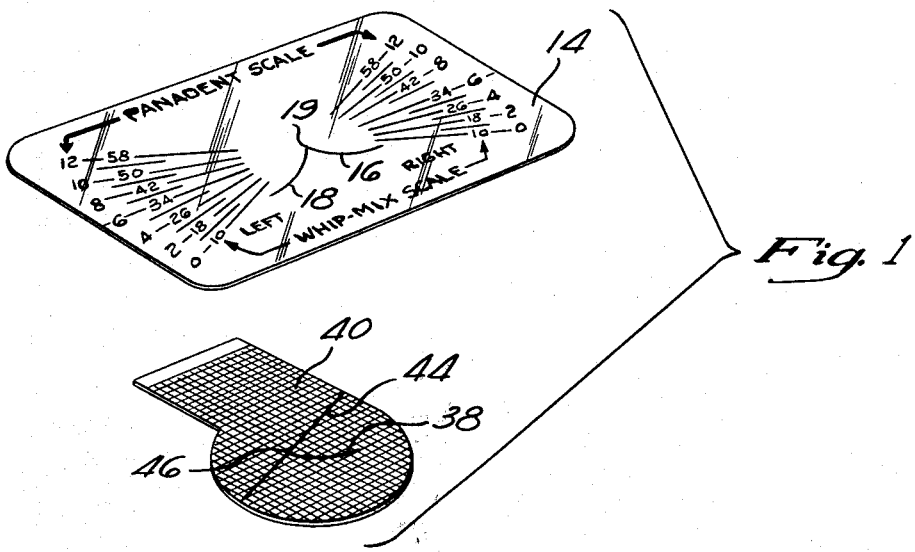
FIG. 1 is a perspective view of the tool of the invention and a recording of a patient's jaw movement, with the tool being spaced above the recording.
Figure 2:
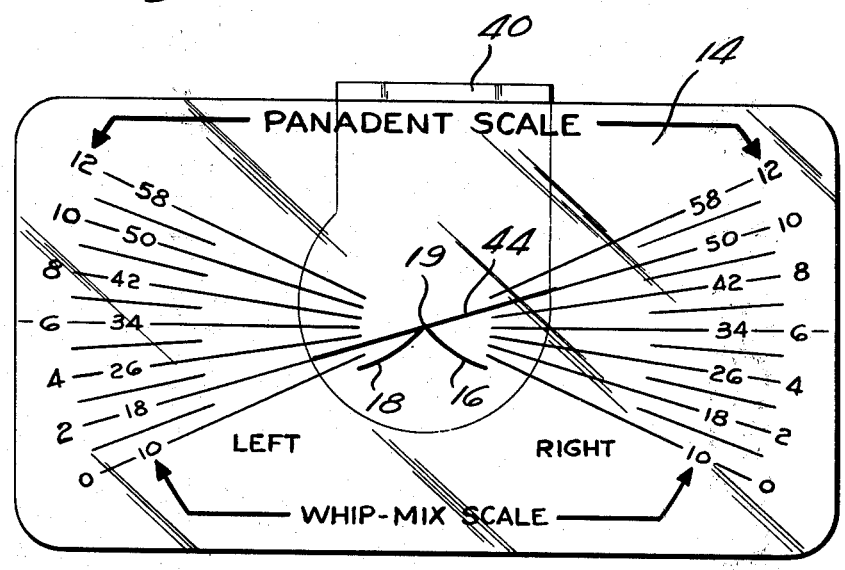
FIG. 2 is a plan view of the tool with the right curve on the tool aligned with the curve on the recording and with the reference line on the recording extending adjacent one of the scale lines on the tool.

Referring back to the tool of FIGS. 1 and 2, it may be seen that a plurality of scale reference lines are formed on the tool extending radially outwardly from the intersection 19 of the two curves 16 and 18 which corresponds to the patient's hinge axis. A series of numbered lines are provided for each of the two curves. The outer set correspond with settings on an articulator sold under the trademark PANADENT, and the inner series correspond with the markings on a product sold under the mark WHIP-MIX.

In use, a recording 38 of a patient's protrusive jaw movement is made on a grid sheet 40 in a manner explained in U.S. Pat. No. 4,034,475. A reference line 44 also formed on the sheet intersects the curve 38 at a point 46 representing the patient's hinge axis. The line further extends through a predetermined point on the patient's nose, which is located by use of an upper recording frame, as described in the above-referenced patent. This line is in a reference plane that is very important in that such reference plane is correlated with a plane in the articulator that makes recording of the jaw movement meaningful. The corresponding plane in the articulator is through hinge axis 32; and through a point in the upper frame of the articulator when the frames are in centric position. This is further explained in the above mentioned patent.

After the jaw movement recording, the record sheet 40 is removed from its support and placed on a convenient flat surface. The tool 14 is placed over the record sheet 40 as shown in FIG. 2, and the right curve 16 formed on the tool is aligned with the curve 38 on the record sheet 40. The hinge axis 46 on the record sheet is also aligned with the corresponding point 19 on the tool. As can be seen the reference line 44 on the record sheet extends towards the scale or lines on the tool and it is a simple matter to see at a glance the orientation of the reference line 44 on the record sheet with respect to the closest scale line on the tool. In the illustration given, the record sheet reference line 44 is oriented very close to the line identified by the number 10 on the PANADENT scale on the tool, and the number 50 on the WHIP-MIX scale.

The scale on the articulator shown in FIG. 3 corresponds to the PANADENT scale on the tool, so that if the reference line on the patient's recording aligns with the reference line 10 on the tool, it is a simple matter to rotate the guide block in the articulator so that the upper edge 34 of the guide block is oriented with the numeral 10.

It should be noted that the upper edge 34 of the guide block 20 does not pass through the stylus axis 32, and the scale lines on the articulator similarly do not extend radially outwardly from the hinge axis. Instead, the upper edge of the guide block is used as reference surface and the lines formed on the articulator scale are oriented so that as the guide block is pivoted around the hinge axis 28, the upper edge of the guide block will be properly oriented to the scale line to which it is aligned. The choice of the upper edge as the reference line is arbitrary, and in the arrangement illustrated, the upper edge 34 is approximately parallel to the horizontal reference plane of the articulator when the upper edge 34 is aligned with the numeral 6 on the articulator scale. The setting of the articulator by use of the tool of the invention is very accurate and easily and directly obtained.

Most articulators currently on the market that include rotatably mounted guide blocks have a scale for the orientation of the guide block and a reference surface or line on the guide block which is used for this purpose. Thus, a particular tool must be designed to fit the articulator with which it is to be used. The WHIP-MIX articulator can accommodate the guide block 20 illustrated in FIG. 3, with the upper edge of the guide block being used as the aligning reference; however, its scale is marked with numerals corresponding to the inner arc of numerals shown on the tool. There is a tendency to think of these lines as representing degrees of an angle and then think of the patient's protrusive path as having a certain angle with respect to a plane of reference. However, this is not completely accurate in that the protrusive path is almost always a curve, and thus a tangent to the curve changes with the tangent point. Thus, the numbers shown on the tool for the WHIP-MIX articulator are not intended to represent degrees but merely to correspond to the numerals on the WHIP-MIX articulator.

What is claimed is:

1. Dental apparatus comprising:
    a dental articulator including a lower frame having a pair of spaced styluses defining a hinge axis and an upper frame having a pair of guide blocks, each having an opening for receiving one of said styluses with the opening having an upper wall determining the protrusive movement of the upper frame relative to the lower frame;
    a recording of a patient's jaw movement protrusive path including a reference line formed thereon which is correlated to a reference plane on the articulator; and
    a thin flat transparent tool having a curve marked thereon which corresponds to the curvature of the protrusive path of the center of one of said styluses when the stylus is moved in engagement with the upper wall of one of the guide blocks, said tool further having means defining one or more scale lines marked thereon oriented to intersect said curve, with the intersection representing the articulator hinge axis of curvature when the guide blocks are positioned in centric relation with respect to the styluses, said tool further having markings thereon which correspond to markings on the articulator for indicating the angle at which said guide block should be set, whereby said tool curve may be aligned with said recording path and the angular orientation of said recording reference line with respect to said scale lines may be observed and utilized to set the angular orientation of said one guide block in the articulator.

2. The apparatus of claim 1 wherein said tool includes a second curve formed thereon corresponding to the curvature of the upper wall of the articulator other guide block, and means defining one or more scale lines oriented with respect to said second curve to be used in setting the orientation of the other articulator guide block, said tool curves intersecting at a point representing the articulator hinge axis, with one curve at its scale lines being located on one side of one tool surface and the other curve and its scale line being located on the other side of said one tool surface.

3. A method of setting a dental articulator having a lower frame with a pair of styluses defining a hinge axis and an upper frame having a pair of rotatably mounted guide blocks each having an opening for receiving one of said styluses including an upper wall which guides the protrusive movement of one of said styluses, said method comprising the steps of:
    providing on a tool a curve corresponding to the curvature of the protrusive path of one of said styluses as it moves in one of said guide block openings engaging the upper wall of the opening, said curve including means indicating the hinge axis of said path; and
    providing indicia on said tool related to said curve in a manner corresponding to indicia on said articulator upper frame representing different angular settings of said block in the articulator upper frame so that the articulator guide blocks may be set by aligning the curve on said tool with the curve on a recording of a patient's protrusive path, with a representation of the hinge axis on the patient's curve and the hinge axis on the tool curve being aligned, observing the angular orientation of a reference line on the patient's recording with respect to said indicia on said tool, and using said observed angular orientation to set the angular orientation of said guide block.

4. A method of properly orienting a guide in a dental articulator utilizing a recording having a path of a patient's jaw movement and a reference line marked on the recording which is correlated with a reference plane in said articulator, said guide having a curved surface which controls the operational movement of the articulator, said method comprising:
    positioning a tool adjacent said recording and directly aligning a curve on said tool with the path on said recording, the curve on said tool representing said curved surface on said guide, said tool having means defining one or more scale lines formed thereon representing reference lines with respect to said tool curve;
    observing the orientation of said recording reference line with respect to a tool scale line; and
    utilizing said observation to position directly the guide in said articulator;
    said guide being mounted in the upper frame of a dental articulator, said guide having an opening which receives one of two styluses on a lower frame of the articulator that define the hinge axis of the articulator, the upper wall of said guide opening being said guide curved surface guiding the movement of one of said styluses in said opening during protrusive movement of the stylus relative to the guide, said recording reference line intersects said curve at a point representing the patient's jaw hinge axis, said recording path representing the patient's protrusive path and the curve on said tool representing the protrusive path of said stylus in said opening, with the stylus engaging the upper wall of said opening, said aligning including aligning a point on said tool curve representing the hinge axis of said tool curve with the hinge axis of the recording path.

* * * * *